US005298017A

United States Patent [19]
Theeuwes et al.

[11] Patent Number: 5,298,017
[45] Date of Patent: Mar. 29, 1994

[54] LAYERED ELECTROTRANSPORT DRUG DELIVERY SYSTEM

[75] Inventors: Felix Theeuwes, Los Altos Hills; J. Richard Gyory; Ronald P. Haak, both of San Jose, all of Calif.

[73] Assignee: ALZA Corporation, Palo Alto, Calif.

[21] Appl. No.: 998,154

[22] Filed: Dec. 29, 1992

[51] Int. Cl.⁵ ............................................. A61N 1/30
[52] U.S. Cl. ................................. 604/20; 607/149; 607/152
[58] Field of Search .................. 128/798, 802, 803; 604/70

[56] References Cited

U.S. PATENT DOCUMENTS

| | | | |
|---|---|---|---|
| 3,991,755 | 11/1976 | Vernon et al. | 128/172.1 |
| 4,141,359 | 2/1979 | Jacobsen et al. | 128/172.1 |
| 4,250,878 | 2/1981 | Jacobsen et al. | 128/207.21 |
| 4,325,367 | 4/1982 | Tapper | 128/207.21 |
| 4,383,529 | 5/1983 | Webster | 604/20 |
| 4,391,278 | 7/1983 | Cahalan et al. | 128/640 |
| 4,398,545 | 8/1983 | Wilson | 128/798 |
| 4,474,570 | 10/1984 | Ariura et al. | 604/20 |
| 4,702,732 | 10/1987 | Powers et al. | 604/20 |
| 4,722,726 | 2/1988 | Sanderson et al. | 604/20 |
| 4,927,408 | 5/1990 | Haak et al. | 604/20 |
| 4,973,303 | 11/1990 | Johnson et al. | 604/20 |
| 5,057,072 | 10/1991 | Phipps | 604/20 |
| 5,087,240 | 2/1992 | Sibalis | 604/20 |
| 5,162,043 | 11/1992 | Lew et al. | 604/20 |

FOREIGN PATENT DOCUMENTS 410009 10/1933 United Kingdom .

OTHER PUBLICATIONS

Tyle, Praveen, "Drug Delivery Devices, Fundamentals and Applications", 1988, pp. 421–454.

Primary Examiner—C. Fred Rosenbaum
Assistant Examiner—Michael Rafa
Attorney, Agent, or Firm—Robert Scott Meece; D. Byron Miller; Steven F. Stone

[57] ABSTRACT

An iontophoretic agent delivery device, having a layered structure and peripheral insulation, wherein ion transport occurs through two opposing surfaces of said device. The device is especially suited to agent delivery through body surfaces exposed to body fluids. A method of delivering an agent through a body surface exposed to body fluids is also disclosed.

25 Claims, 3 Drawing Sheets

LAYERED ELECTROTRANSPORT DRUG DELIVERY SYSTEM

TECHNICAL FIELD

This invention relates to transmucosal and transdermal drug delivery. More particularly, this invention relates to transmucosal and transdermal drug delivery systems which utilize electrical current to facilitate drug delivery. Still more particularly, this invention relates to drug delivery in an environment exposed to body fluids, and optionally, drug delivery employing system contact with two opposing body surfaces.

BACKGROUND ART

In the past, iontophoresis has been defined as the introduction, by means of electric current, of ions of soluble salts into the tissues of the body for therapeutic purposes. Iontophoretic devices for delivering ionized drugs through the skin have been known since the early 1900's. Deutsche UK Pat. No. 410,009 (1934) describes an iontophoretic device which overcame one of the disadvantages of such earlier devices, namely that the patient was required to be immobilized near the source of the electric current. The Deutsche device was powered by a galvanic cell formed from the electrodes and the material containing the drug to be delivered. The galvanic cell produced the current necessary for iontophoretic delivery of the drug. Thus, this device permitted the patient freedom of movement during iontophoretic drug delivery.

Today, iontophoretic drug delivery is not limited to delivery of ions into the body via electrical current. For example, iontophoretic devices can deliver an uncharged drug into the body via electroosmosis. Electroosmosis is defined as the transdermal flux of a liquid solvent containing an uncharged drug or agent induced by an electric field. Thus, the terms "iontophoretic" and "electrotransport", as used herein, include, but are not limited to, (1) the delivery of charged drugs or agents by electromigration, (2) the delivery of uncharged drugs or agents by the process of electroosmosis, (3) the delivery of charged drugs or agents by the combined processes of electromigration and electroosmosis, (4) the delivery of a mixture of charged and uncharged drugs or agents by the combined processes of electromigration and electroosmosis, and (5) the delivery of agents through pathways created in situ by electroporation. Therefore, a general definition of "iontophoresis" or "electrotransport", as used herein, is the transport of a substance induced or enhanced by the application of an electric potential.

A number of U.S. patents have issued in the iontophoretic agent delivery field. For example, Vernon et al, U.S. Pat. No. 3,991,755; Jacobsen et al, U.S. Pat. No. 4,141,359; Wilson, U.S. Pat. No. 4,398,545; and Jacobsen, U.S. Pat. No. 4,250,878 disclose examples of iontophoretic devices and applications thereof. The iontophoresis process has been useful in the transdermal administration of medications or drugs including lidocaine hydrochloride, hydrocortisone, fluoride, penicillin, dexamethasone sodium phosphate, and insulin, among others. Perhaps the most common use of iontophoresis is in diagnosing cystic fibrosis by delivering pilocarpine salts iontophoretically. The pilocarpine stimulates sweat production; the sweat is collected and analyzed for its chlorine content to detect the presence of the disease.

In presently known iontophoretic devices, at least two electrodes are required. Both electrodes are located in intimate electrical contact with some portion of the skin, nails, or other membrane surface of the body, such that chemical species transport through a body surface is accomplished. One electrode, called the active or donor electrode, is the electrode from which the ionic agent, medication, drug or drug precursor is delivered into the body. The other electrode, termed the counter or return electrode, serves to close the electrical circuit through the body. For example, if the ionic agent to be delivered is positively charged, i.e. a cation, then the anode will be the active or donor electrode, while the cathode serves to complete the circuit. Alternatively, if the ionic agent is negatively charged, i.e. an anion, the cathode will be the donor electrode. Additionally, both the anode and cathode may be used to deliver drugs if both anionic and cationic drug ions are to be delivered. Thus, a complete electrical circuit is formed from electrical contact of the power source to the donor electrode, the donor electrode to the body, the body to the counter electrode, and the counter electrode to the power source.

Iontophoretic delivery devices generally require a reservoir or source of the beneficial agent to be delivered to the body. Examples of such agent reservoirs include a pouch or cavity as described in the previously mentioned Jacobsen patent, U.S. Pat. No. 4,250,878, a porous sponge or pad as disclosed in Jacobsen et al patent, U.S. Pat. No. 4,141,359, and a preformed gel body as described in the Webster patent, U.S. Pat. No. 4,383,529, and the Ariura et al patent, U.S. Pat. No. 4,474,570. Such drug reservoirs are electrically connected to the anode or the cathode of an iontophoretic device to provide a fixed or renewable source of one or more desired agents.

Typically, self-contained iontophoretic delivery devices are designed for contact with only one body surface, such as with electrotransport devices which are placed on the surface of a patient's skin. Structurally, the counter and donor electrodes are usually positioned side by side separated by an insulator, both electrodes being in ion transmitting relation with the same body surface on the same face of the device. This type of electrotransport device is not ideally suited to an environment exposed to body fluids, because of possible short circuiting between the electrodes and/or agent reservoirs via the body fluid. Exemplary of such environments are the oral, nasal, vaginal, ocular and anal cavities. If short-circuiting occurs in such an environment, the iontophoretic agent delivery device merely delivers the agent into the body fluid, e.g. the saliva, and not through the body surface, e.g. buccal membrane, for transport into the blood stream.

Another major issue in iontophoretic delivery systems is the power source. Typically, the power source represents a significant portion of the system cost. In addition, in self-contained systems, the power source is usually formed from one or more batteries having limited useful lives. Thus, a continuing goal in the design of iontophoretic delivery systems is the reduction of power requirements, for example, by reducing the resistance to current flow. Since the major electrical resistance is represented by the two layers of skin through which current typically flows in prior art systems, a reduction in this resistance, resulting in a corresponding reduction in power requirements, would be highly desirable.

Thus, there is a need for device for iontophoretic agent delivery through a mucosal membrane which minimizes the probability of short-circuiting when exposed to body fluids. In addition, there is a further need for a device suitably shaped for iontophoretic agent delivery through two opposing body surfaces. A further need exists for reduction of the cross-sectional area required for an iontophoretic system at a desired agent delivery rate and for reduction of the power requirements for an iontophoretic agent delivery system.

DISCLOSURE OF THE INVENTION

Solution of the above-disclosed needs along with other advantages of this invention will become apparent from the disclosure of the invention wherein a laminated iontophoretic device for delivering an agent through at least one body surface which, in the natural in vivo state, is exposed to a body fluid. The device has a plurality of essentially parallel layers, including (a) a counter electrode layer; (b) a donor electrode layer in electrical contact with the counter electrode layer; and (c) a donor reservoir layer comprising an agent to be delivered, and having a major surface which is adapted to be placed in agent transmitting relation with the body surface. The donor reservoir layer is in electrical contact with the donor electrode layer. The donor electrode layer is positioned between the counter electrode layer and the donor reservoir layer. A peripheral insulating means electrically insulates said donor electrode layer and said donor reservoir layer from body fluids which are in electrical contact with said counter electrode layer via a path not including a body surface.

In addition, this invention relates to an improved method of iontophoretic agent delivery, through a body surface which, in its natural in vivo state, is exposed to a natural body fluid. This method is characterized by use of the apparatus described above.

BRIEF DESCRIPTION OF THE DRAWINGS

The invention will be described in further detail with reference to the accompanying drawings wherein.

MODES FOR CARRYING OUT THE INVENTION

The present invention relates to a transmucosal or transdermal agent delivery system. A transdermal agent delivery system, as used herein, refers to a device for administering chemical species, typically a pharmaceutical agent or drug, through the skin. Similarly, a transmucosal system refers to agent delivery through a mucosal membrane. The terms "transdermal" and "transmucosal" will be used interchangeably herein. More specifically, the delivery system of the present invention is a device which delivers an agent (e.g. a drug) transdermally or transmucosally under the influence of an electric potential. Such devices are referred to herein as electrotransport or iontophoretic systems. Electrotransport, or iontophoretic, drug delivery systems utilize electrical potential to increase the drug delivery driving force, thereby increasing the flux or rate of drug delivery over passive, or non-electrically assisted, transdermal delivery systems which deliver drug through the skin by diffusion.

Figure 1:
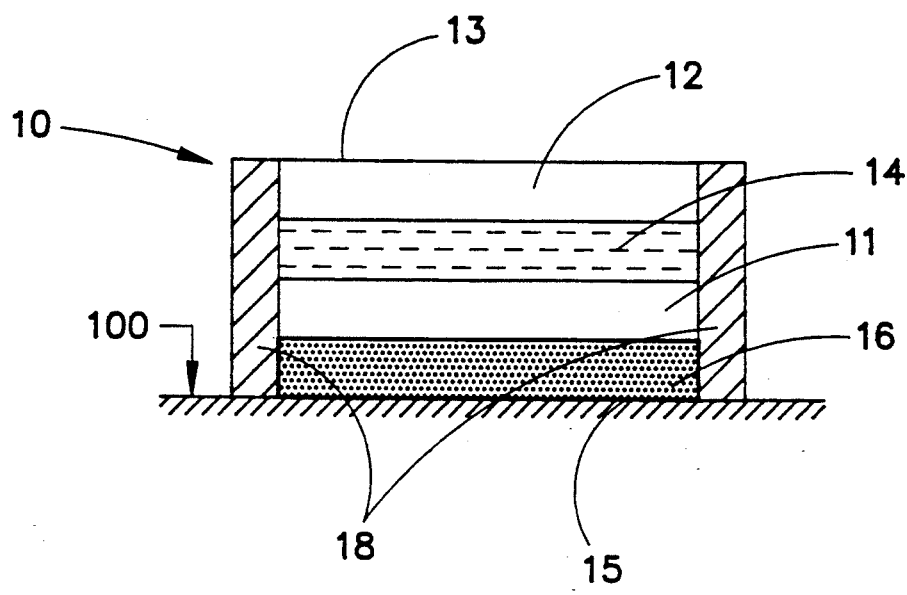
FIG. 1 is a schematic cross sectional view of one embodiment of the electrotransport transmucosal system of this invention having a counter electrode, a power source, a donor electrode, a donor agent reservoir, and peripheral electrical insulation.

One embodiment of the electrotransport system of the present invention, designated by reference numeral 10, is shown in FIG. 1. System 10 includes two current conducting members, referred to herein as a donor electrode 11 and a counter electrode 12. Counter electrode 12 has an exposed surface 13 which is adapted to be placed in electrical contact with the natural body fluid present in the in vivo environment of body surface 100. System 10 also includes a source of electrical power 14 which may optionally include an current controlling circuitry and a donor reservoir 16, which is adapted to be placed in drug transmitting relation with a body surface 100 (e.g. a buccal membrane). The donor reservoir may contain an ion conductive adhesive on the ion-transmitting face or may have such an adhesive laminated thereon. Further, system 10 includes an insulating member 18 to prevent a short circuit between the electrodes and/or reservoir.

The counter electrode 12 is in electrical contact with the optional power source 14 (e.g. a small button cell battery). Although power source 14 is schematically depicted as a single homogenous layer, it will be readily appreciated by those skilled in the art that layer 14 may include one or more batteries connected in parallel or in series as well as electronic circuitry for controlling the amplitude, frequency, duty cycle, etc. of the electrical current generated by the power source. In a similar manner, the donor electrode 11 is also in electrical contact with the power source 14 and is positioned between the agent-containing reservoir 16 and the power supply 14. The electrical insulating member 18 peripherally surrounds the electrotransport device 10 such that two major opposing electrochemically- active exposed surfaces 13 and 15 are formed. Thus, in order for device 10 to function, surface 15 of agent reservoir 16 must be placed in agent transmitting relation with a body surface 100. Furthermore, reservoir 16, donor electrode 11 and power source 14 must be electrically isolated from the natural body fluid present adjacent to body surface 100. Electrical isolation is accomplished by the insulating member 18 which prevents a short-circuit between (1) agent reservoir 16, power supply 14, or donor electrode 11 and (2) counter electrode 12 by way of the natural body fluid without completing an electrical circuit pathway traversing body surface 100. Thus, a complete circuit is formed in FIG. 1 from the following elements connected in series: counter electrode 12; power source 14; donor electrode 11; donor agent reservoir 16; body surface 100; natural body fluid; and counter electrode 12.

As is clearly shown in FIG. 1–4, each of the drug reservoir 16, donor electrode 11, counter electrode 12, optional power source 14 and optional counter agent reservoir 22 represent one separate and distinct cross-sectional layer of the device. The electrotransport device of the present invention comprises a single laminated stacked structure of multiple essentially parallel elements or layers, having two opposing surfaces for electrical contact with opposing body surfaces or a body surface and a natural body fluid (e.g. saliva). The term "laminate" is used herein to describe layers of material firmly united by adhesive, compression molding, heating, or other means. "Essentially parallel layers", as used herein, refers to the layered structure of the devices shown in FIG. 1–4. It is not essential that the surfaces of each layer be exactly parallel to each other. The components of the device are arranged such that ion transport occurs through two major opposing surfaces. Thus, the electrotransport system of this invention has all elements in a single multilayered stack as opposed to conventional electrotransport system designs, wherein the counter and donor electrode assemblies are positioned adjacent one other (i.e. in side-by-side relation) on a single body surface through which agent transport occurs. See, for example, Ariura et al, U.S. Pat. No. 4,474,570 and Haak et al, U.S. Pat. No. 4,927,408.

Figure 2:
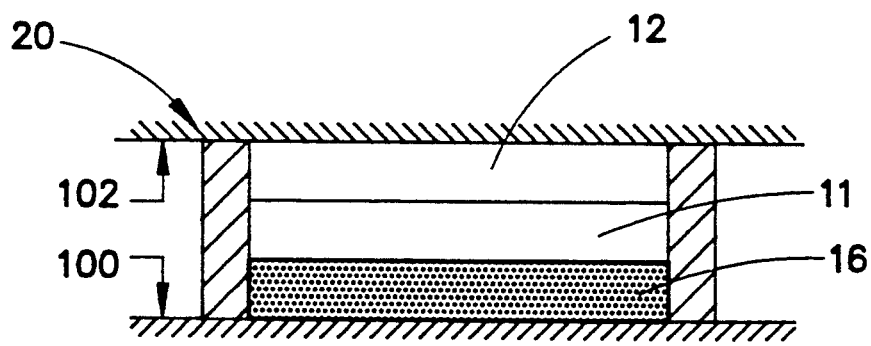
FIG. 2 is a schematic cross sectional view of another embodiment of the electrotransport transmucosal system of this invention having a counter electrode and donor electrode forming a galvanic couple, a donor agent reservoir, and peripheral electrical insulation.

Typically, one of the two opposing surfaces in the single multilayered structure is the surface 15 of the drug reservoir 16. Usually, the other of the two opposing surfaces is the surface 13 of a counter electrode 12 or optional counter agent reservoir 22 (as shown in FIG. 2) containing an electrolyte salt. Other layers, such as rate-controlling membrane, an agent-permeable adhesive layer, or an ion-permeable adhesive layer may constitute the final layer of an exposed face of the device. Regardless of the final layer on the drug transport surface 15, this surface is shaped or adapted so as to conform generally to the selected body surface 100 through which drug delivery will occur. Proper shaping of the surface 15 assists in maintaining good electrical contact between device 10 an body surface 100, thereby aiding in preventing short-circuiting in body areas exposed to ion-conducting body fluids.

Since the anodic and cathodic components of the electrotransport system of this invention are arranged in a stacked fashion relative to the body surface, the cross-sectional area of the device is advantageously reduced when compared with devices having adjacent anodic and cathodic components. This feature is important in body locations having limited surface areas for drug delivery, such as the buccal or sublingual areas.

FIG. 2 illustrates another embodiment of the present invention wherein the electrodes are comprised of dissimilar materials (e.g. metals) and form a galvanic couple. Typical materials which provide such a galvanic couple include using a zinc donor electrode 11 and a silver/silver chloride counter electrode 12. Such a combination can provide a potential of about one volt. In this embodiment, the galvanic couple generates sufficient power to operate the device without a separate power source. In addition, device 10 may be powered by a combination of a galvanic couple formed by electrodes 11 and 12 and an independent power source 14 (e.g. one or more batteries). Furthermore, the ion transport pathway of the FIG. 2 embodiment is depicted as including a second body surface 102, opposite body surface 100 through which drug ion is transported. Exemplary of a body location having opposing mucosal membrane surfaces is the oral area between the cheek and gum.

Figure 3:
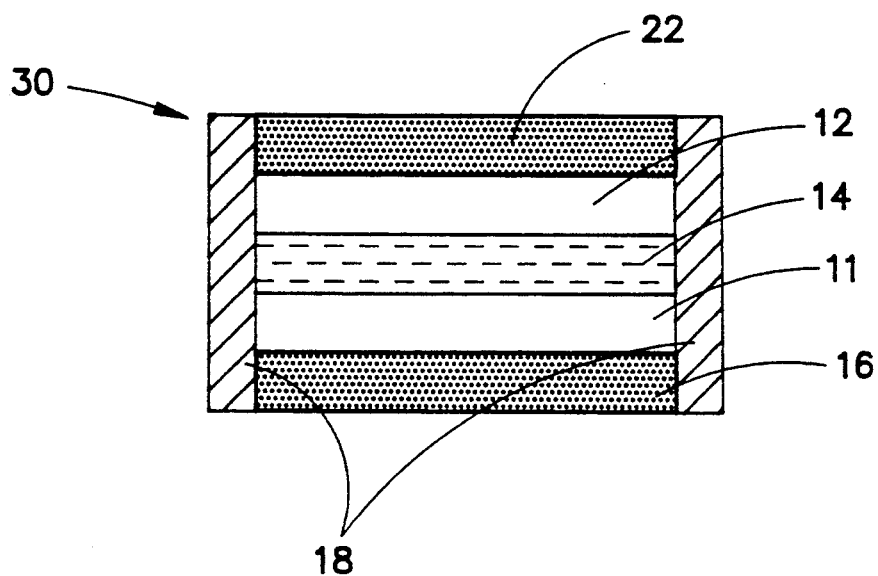
FIG. 3 is a schematic cross sectional view of another embodiment of the electrotransport transmucosal system of this invention having an optional counter agent reservoir.

A further embodiment of the present invention is the addition of an electrolyte-containing counter electrode reservoir layer 22, as illustrated in FIG. 3. Counter reservoirs may be helpful as electrical current distribution members. Also, buffers may be added to the counter reservoir to maintain acceptable pH levels. This counter reservoir layer 22 is positioned adjacent to, and in electrical contact with, the counter electrode layer 12, on the side opposite the power source layer 14. A commonly used electrolyte salt is sodium chloride.

Figure 4:
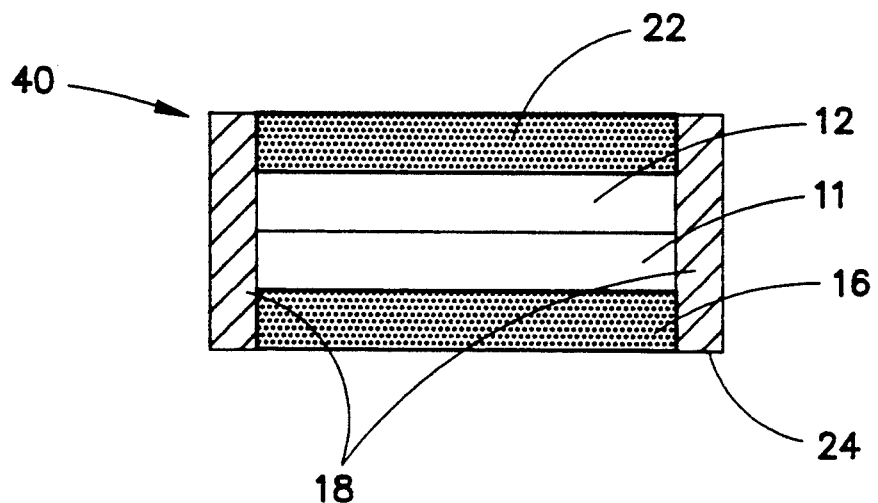
FIG. 4 is a schematic cross sectional view of another embodiment of the electrotransport transmucosal system of this invention having an adhesive on one edge of the peripheral insulation layer.
Figure 5:
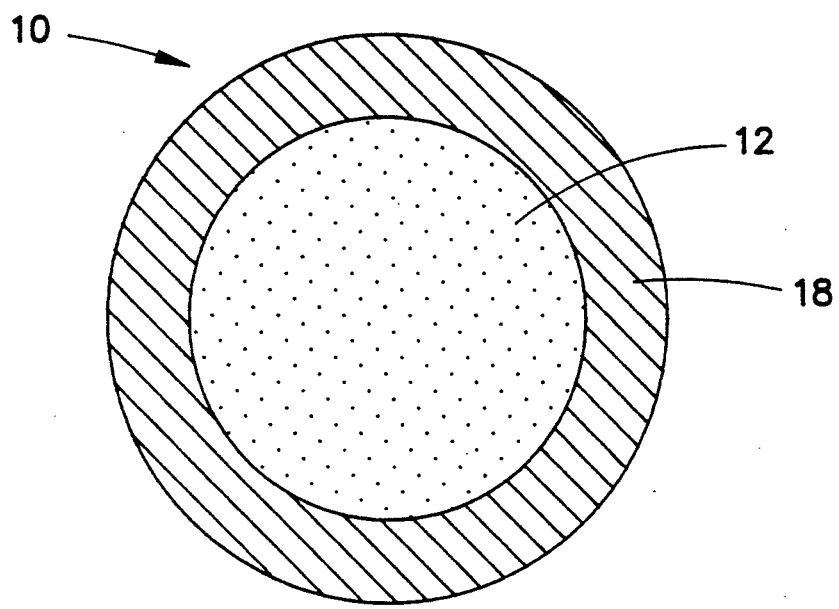
FIG. 5 is a schematic bottom face view of the device shown in FIG. 1, wherein the electrotransport system is circular.
Figure 6:
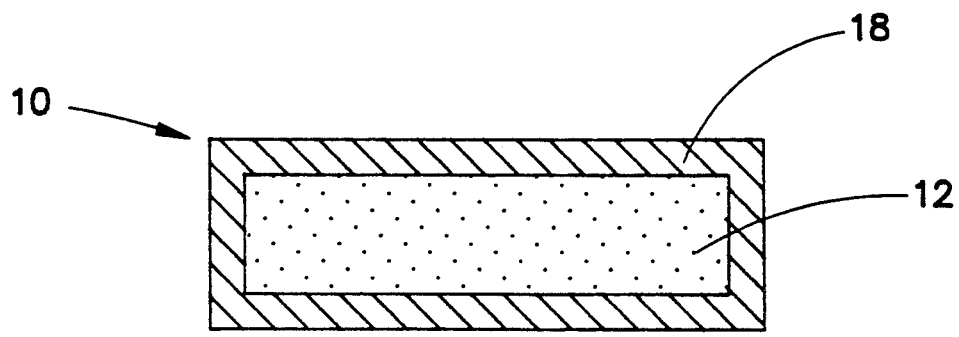
FIG. 6 is a schematic bottom face view of the device shown in FIG. 1, wherein the electrotransport system is rectangular.

FIG. 4 depicts schematically another embodiment of the present invention wherein a contact adhesive 24 is applied on insulator 18 of surface 15. This adhesion must be sufficient to prevent short-circuiting of drug ion transport through surrounding body fluids and external to body surface 100. A separate adhesive 24 may be unnecessary when the donor reservoir matrix is chosen such that it adheres to the body surface 100. For example, donor reservoir 16 may be formed of a hydrophilic polymer matrix which, upon contact with body fluids (e.g. saliva), forms a hydrogel having adhesive properties.

The cross-sectional size of the electrotransport transmucosal system of this invention can vary from about 1 cm$^2$ to about 25 cm$^2$. The preferred system, however, will have a size within the range of about 1 to about 5 cm$^2$, due to the limited space available in mucosal areas of the body, such as the buccal or sublingual areas.

BIOLOGICALLY ACTIVE AGENTS

This invention has utility in connection with the delivery of drugs within the broad class normally delivered through the body surfaces and membranes, including skin, mucosa and nails. As used herein, the expressions "biologically active agent", "agent" or "drug" are used interchangeably and are intended to have their broadest interpretation as any substance which is delivered to a living organism to produce a desired, usually beneficial, effect. In general, this includes therapeutic agents in all of the major therapeutic areas including, but not limited to, anti-infectives such as antibiotics and antiviral agents; analgesics such as fentanyl, sufentanil, and buprenorphine, and analgesic combinations; anesthetics; anorexics; antiarthritics; antiasthmatic agents such as terbutaline; anticonvulsants; antidepressants; antidiabetics agents; antidiarrheals; antihistamines; antiinflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics including gastrointestinal and urinary; anticholinergics; sympathomimetrics; xanthine derivatives; cardiovascular preparations including calcium channel blockers such as nifedipine; beta-agonists such as dobutamine and ritodrine; beta blockers; antiarrythmics; antihypertensives such as atenolol; ACE inhibitors such as ranitidine; diuretics; vasodilators including general, coronary, peripheral and cerebral; central nervous systems stimulants; cough and cold preparations; decongestants; diagnostics; hormones such as parathyroid hormones; hypnotics; immunosuppressives; muscle relaxants; parasympatholytics; parasympathomimetrics; prostaglandins; proteins; peptides; psychostimulants; sedatives and tranquilizers.

More specifically, it is anticipated that this invention will prove useful in the controlled delivery of baclofen, beclomethasone, betamethasone, buspirone, cromolyn sodium, diltiazem, doxazosin, droperidol, encainide, fentanyl, hydrocortisone, indomethacin, ketoprofen, lidocaine, methotrexate, metoclopramide, miconazole, midazolam, nicardipine, piroxicam, prazosin, scopolamine, sufentanil, terbutaline, testosterone, tetracaine, and verapamil.

Specifically, in one embodiment, this invention is useful in connection with the delivery of drugs through mucosal membranes such as buccal, vaginal, and rectal membranes, all of which are exposed to natural body fluids (e.g. saliva) in their natural in vivo state. In rectal applications, the system would preferably be shaped similar to a suppository, with opposing electrode surfaces parallel to the longitudinal axis of the body. The therapeutic agents suitable for delivery through the buccal membranes within the oral cavity include, without limitation, antifungal agents, antiviral agents, antiinflammatory agents, and sialagogue.

The invention is particularly useful in the controlled delivery of peptides, polypeptides, proteins, or other macromolecules difficult to deliver transdermally or transmucosally because of their size. These macromolecular substances typically have a molecular weight of at least about 300 daltons, and more typically, a molecular weight in the range of about 300 to 40,000 daltons. Examples of peptides and proteins which may be delivered using the device of the present invention include, without limitation, LHRH, LHRH analogs such as buserelin, goserelin, gonadorelin, naphrelin, naturetin, leuprolide, GHRH, GHRF, insulin, insulinotropin, heparin, calcitonin, octreotide, endorphin, TRH, NT-36 (chemical name: N-[[(s)-4-oxo-2-azetidinyl]carbonyl]-L-histidyl-L-prolinamide], liprecin, pituitary hormones (e.g., HGH, HMG, HCG, desmopressin acetate), follicle luteoids, α-ANF, growth factor releasing factor (GFRF), β-MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF'S, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 antitrypsin (recombinant), and TGF-beta.

Examples of agents likely to be delivered to the oral cavity include, without limitation, oxygenating agents, octenidine, decapinol, triclosan, nystatin, chlortrimazole, fluconazole, miconazole, ketoconazole, itraconazole, amphotericin B, acyclovir, idoxuridine, ibuprofen, flurbiprofen, ketoprofen, naproxen, aspirin, piroxicam, hydrocortisone, betamethasone, dexamethasone, beclomethasone dipropionate, fluocinonide, pilocarpine, and retin A.

ELECTRODES

Donor electrode 11 and counter electrode 12 are comprised of electrically conductive material such as a metal. For example, electrodes 11 and 14 may be formed from metal foil, metal screen, metal deposited or painted on a suitable backing, calendaring, film evaporation, or by mixing the electrically conductive material in a polymer binder matrix. Examples of suitable electrically conductive materials include carbon, graphite, silver, zinc, silver chloride, aluminum, platinum, stainless steel, gold and titanium. For example, the anodic electrode may be composed of silver and the cathodic electrode may be composed of silver chloride. Silver is preferred over other metals because of its relatively low toxicity to mammals. Silver chloride is preferred because the electrochemical reduction reaction occurring at the cathode produces chloride ions which are prevalent in, and non-toxic to, most animals.

Alternatively, electrodes 11 and 14 may be formed of a polymer matrix containing a conductive filler such as a metal powder, powdered graphite, carbon fibers, or other known electrically conductive filler material. The polymer based electrodes may be made by mixing the conductive filler in a polymer matrix, preferably a mixture of hydrophilic and hydrophobic polymers. The hydrophobic polymers provide structural integrity, while the hydrophilic polymers may enhance ion transport. For example, zinc powder, silver powder, silver chloride powder, powdered carbon, carbon fibers and mixtures thereof can be mixed in a hydrophobic polymer matrix, with the preferred amount of conductive filler being within the range of about 30 to about 90 volume percent, the remainder being the polymer matrix or other inert additives.

BODY SURFACES AND FLUIDS

The term "body surface" as used herein describes any biological membrane including skin, nails, and mucosal membranes. The term "body fluids" as used herein refers to natural biological fluids produced by an animal (e.g. a human) found adjacent to the body surface through which the agent is being delivered by electrotransport in the natural in vivo state of the body surface. For example, the electrotransport system of this invention is especially well adapted to deliver agent through the oral mucosal membranes, i.e. buccal and sublingual areas, which are nearly continuously exposed to natural body fluids such as saliva and/or mucus. Other applications of this electrotransport system include insertions into body cavities such as rectal and vaginal area, or use as an implant, i.e. electrotransport system insertion into tissue via a surgical procedure.

ELECTRICAL POWER SOURCE

The electrotransport system of this invention can be powered in various manners, depending upon the requirements of the system. If the counter and donor electrodes are of dissimilar metals or have different half cell reactions, it is possible for the system to generate its own electrical power. This embodiment is illustrated in FIG. 2, as described above. Typical materials which provide a galvanic couple include a zinc donor electrode and a silver chloride counter electrode. Such a combination will produce a potential of about one volt. When a galvanic couple is used, the donor electrode 11 and counter electrode 12 are integral portions of the power generating process. Such a galvanic couple powered system, absent some controlling means, activates automatically when body tissue and/or fluids form a complete circuit with the system. There exist numerous other examples of galvanic couple systems potentially useful in the present invention.

Standard electrochemical reactions and the respective reduction potentials are well known in the art. For instance, see the CRC Handbook of Chemistry and Physics, pp. D133-D138, 62$^{nd}$ edition (1981-1982), which is incorporated herein by reference. For example, use of a zinc anode, wherein the following reaction occurs:

$$Zn = Zn^{++} + 2e^{-} \quad E^{o}_{oxidation} = 0.76 \text{ volts}$$

and a silver chloride cathode, wherein the following reaction occurs:

$$AgCl + e^{-} = Ag + Cl^{-} \quad E^{o}_{reduction} = 0.22 \text{ volts}$$

produces a cell voltage of about one volt (0.76+0.22). If the average buccal mucus membrane resistance is about 2 k$\Omega$-cm$^2$ (R) and the membrane resistance is the predominant impedance component, then, based on Ohm's Law (V=IR), a current of about 0.5 mA/cm$^2$ (I) could be achieved without the use on an external power supply. This is based on the assumption that there is negligible resistance within the donor and counter electrodes and respective reservoirs. In addition, conditions are presumed to be optimal to produce the maximum possible voltage, i.e. the voltage is calculated from the standard electrochemical potentials.

In some instances it may be necessary to augment the power supplied by the galvanic electrode couple. This may be accomplished with the use of a separate electrical power source 14, as shown in FIG. 1. Such a power source is typically a battery or plurality of batteries, connected in series or in parallel, and positioned between the counter electrode 12 and donor electrode 11, such that the donor electrode 11 is connected to one pole of the power source 14 and the counter electrode 12 is connected to the opposite pole. Commonly, one or more 3 volt button cell batteries, such as PANASONIC ® model CR 2025, are suitable to power electrotransport devices.

The electrotransport system of the present invention has a shape and size making it especially well suited for agent delivery through mucosal membranes. It should be noted that such membranes exhibit lower electrical resistances than skin tissue generally. Thus, the electrotransport systems of this invention, when applied to mucosal membranes, have advantageously lower power requirements than systems applied to intact skin. Lower power requirements may enable designs with smaller or fewer batteries or extended use periods.

As mentioned above, power source 14 may include electronic circuitry for controlling the operation of the electrotransport device. Thus, power source 14 may include circuitry designed to permit the patient to manually turn the system on and off, such as with an on-demand medication regime, or to turn the system on and off at some desired periodicity, for example, to match the natural or circadian patterns of the body. A relatively simple controller or microprocessor could control the current at a function of time or could generate complex current waveforms such as pulses or sinusoidal waves. The control circuitry may also include a biosensor and some type of feedback system which monitors biosignals, provides an assessment of therapy, and adjusts the drug delivery accordingly. A typical example is the monitoring of the blood sugar level for controlled administration of insulin.

AGENT RESERVOIRS

The donor agent reservoir layer 16 and optional counter agent reservoir layer 22 can be any material adapted to absorb and hold a sufficient quantity of liquid therein in order to permit transport of agent therethrough by iontophoresis. For example, gauzes, pads or sponges composed of cotton or other absorbent fabric, both natural and synthetic, may be used. More preferably, the matrices of reservoir layers 16 and 22 are composed, at least in part, of one or more hydrophilic polymers. Hydrophilic polymers are typically preferred because water is the preferred ion transport medium and hydrophilic polymers have a relatively high equilibrium water content. Most preferably, the matrices of reservoir layers 16 and 22 are solid polymer matrices composed, at least in part, of hydrophilic polymer. Insoluble hydrophilic polymer matrices are preferred over soluble hydrophilic polymers since the probability of delivering insoluble polymer through the body surface is very low.

The matrix can be cross-linked with the agent components in place such as a silastic matrix, or the polymers can be prefabricated and sorbed with the components from solutions as is the case with cellulose, woven fiber pads and sponges. The agent reservoir layers 16 and 22 can alternately be a gel matrix structure, formed similarly to the polymeric matrix structure wherein the gel is formed of a hydrophilic polymer which is swellable or soluble in water. Such polymers can be blended with the components in any ratio, but preferably represent from a few percent up to about 50 percent by weight of the reservoir. The polymers can be linear or cross-linked. Suitable hydrophilic polymers include copolyesters such as HYTREL ® (DuPont De Nemours & Co., Wilmington,Del.), polyvinylpyrrolidones, polyvinyl alcohol, polyethylene oxides such as POLYOX (Union Carbide Corp.), CARBOPOL ® (BF Goodrich of Akron, Ohio), blends of polyoxyethylene or polyethylene glycols with polyacrylic acid such as POLYOX ® blended with CARBOPOL ®, polyacrylamide, KLUCEL ®, cross-linked dextran such as SEPHADEX ® (Pharmacia Fine Chemicals, AB, Uppsala, Sweden), WATER LOCK ® (Grain Processing Corp., Muscatine, Iowa) which is a starch-graft-poly(sodium acrylate-co-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-Di-Sol (FMC Corp., Philadelphia, Pa.), hydrogels such as polyhydroxylethyl methacrylate (National Patent Development Corp.), natural gums, chitosan, pectin, starch, guar gum, locust bean gum, and the like, along with blends thereof. Of these, polyvinylpyrrolidones are preferred. This list is merely exemplary of the materials suited for use in this invention. Other suitable hydrophilic polymers can be found in J. R. Scott & W. J. Roff, Handbook of Common Polymers (CRC Press, 1971), which is hereby incorporated by reference.

Optionally, the matrices of reservoir layers 16 and 22 may contain a hydrophobic polymer, to improve structural integrity. Preferably the hydrophobic polymer is heat fusible, in order to enhance the lamination of reservoir layers 16 and 22 to adjacent layers. Suitable hydrophobic polymers for use in the reservoir matrices include, but are not limited to, polyisobutylenes, polyethylene, polypropylene, polyisoprenes and polyalkenes, rubbers, copolymers such as KRATON ®, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, 1-methyl pentanol, 2-methyl pentanol, 3-methyl pentanol, 2-ethyl butanol, isooctanol, n-decanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, itaconic acid, N-branched alkyl maleamic acids wherein the alkyl group has 10-24 carbon atoms, glycol diacrylates, and blends thereof. Most of the above-mentioned hydrophobic polymers are heat fusible. Of these, polyisobutylenes are preferred.

The reservoir layer matrices 16 and 22 may be a polymeric matrix structure formed by blending the desired agent, drug, electrolyte, or other component(s), with an inert polymer by such processes as melt blending, solvent casting, tableting, or extrusion. Typically, the donor agent reservoir layer contains a drug to be delivered, while the counter agent reservoir layer contains an electrolyte, e.g. a water soluble biocompatible salt. In addition to the drug and electrolyte, the reservoirs 16 and 22 may also contain other conventional materials such as flavorings, inert fillers, and the like. The counter agent reservoir 22 may contain one or more pharmacologically acceptable salts, such as sodium chloride.

Furthermore, one or more rate controlling membranes (not shown) may be placed between the donor agent reservoir layer 16 and the body surface for controlling the rate at which the agent is delivered or limiting passive agent delivery when the power source is in an "off" mode.

ADHESIVE

While FIG. 4 depicts a separate peripheral adhesive means 24 as an alternate embodiment of the invention, such adhesive may be unnecessary where the donor agent reservoir layer 16 composition displays self-adhering qualities. Suitable self-adhering matrix materials for electrotransport devices include, without limitation, poly(styrenebutadiene) and poly(styrene-isoprene-styrene) block copolymers, and polyisobutylene copolymers. Other suitable self-adhering matrix materials are set forth in the art such as are described in U.S. Pat. Nos. 4,391,278, 4,474,570, and 4,702,732, all of which are incorporated herein by reference.

In selecting an adhesive distinct from the donor reservoir matrix for mucosal areas, several factors should be balanced. For instance, the adhesive must provide sufficient adhesive forces to maintain donor reservoir contact with the mucosal tissue to prevent ion transfer through the body fluid and external to the body surface. Yet, the adhesive forces should not be so strong that mucosal tissue is torn upon removal of the electrotransport device. Other factors to consider in selecting the adhesive include toxicity, irritation and sensitivity, and processability.

The CRC *Critical Review in Therapeutic Drug Carrier Systems*, volume 5, issue 1 (1988), describes some characteristics typical of good bioadhesive polymers. The molecular characteristics of good bioadhesives include (1) the existence of hydrophilic functional groups that can form hydrogen bonds, (2) high molecular weights (e.g. above about 100,000), and (3) mobility and flexibility of the polymer chains.

Exemplary of adhesives suitable for mucosal areas are, without limitation, sodium carboxymethyl cellulose (SCMC); poly(acrylic acid); poly(methyl acrylic acid); copolymers of acrylic acid and related derivatives such as copolymers of acrylic acid/divinylbenzene, methacrylic acid/divinylbenzene, and acrylic acid/2,5-dimethyl-1,5-hexadiene; tragacanth; poly(methyl vinylether co-maleic anhydride); poly(ethylene oxide); methylcellulose; sodium alginate; hydroxypropylmethylcellulose; Karaya gum; methylethylcellulose; soluble starch; gelatin; pectin; poly(vinyl pyrrolidone); poly(ethylene glycol); poly(vinyl alcohol); poly(hydroxyethylmethacrylate); hydroxypropylcellulose; guar gum; hydroxyethylcellulose; Retene; poly(methacrylic acid); copolymers of acrylic acid and divinyl glycol such as POLYCARBOPHIL ® (a polyacrylic acid lightly cross-linked with 0.15%-1.0% divinyl glycol(3,4-dihydroxy-1,5-hexadiene, sold by B. F. Goodrich), and mixtures thereof. The preferred adhesives demonstrate high adhesive forces in order to prevent ion-conduction through the body fluid and external to the body surface. Examples of preferred adhesives include copolymers of acrylic acid and divinyl glycol, SCMC, poly(acrylic acid), tragacanth, poly(methyl vinylether co-maleic anhydride), copolymers of acrylic and methacrylic acids, and mixtures thereof.

INSULATOR

The peripheral insulator 18 prevents direct ion transport between the donor electrode 11 or donor agent reservoir layer 16 and counter electrode layer 12 or counter agent reservoir layer 22 without delivering ions through a body surface. Therefore, the insulator is preferably composed of a relatively electrically non-conducting material which is relatively impermeable to the passage of both ions and water. Preferably, the insulating material is a polymer capable of strong bonding with the reservoir polymer matrix, in order to provide enhanced structural integrity. Polyisobutylenes or ethylene vinyl acetate (EVA), disclosed also with regard to the reservoir matrices, are the preferred insulating materials. The adhesive may be formed as a casing, partially encapsulating the donor and counter electrode to provide mechanical strength to the system.

Having thus generally described our invention, the following examples will illustrate how variations of the above-described parameters provide therapeutically effective electrotransport systems.

EXAMPLE I

One embodiment of the electrotransport system of the present invention has the configuration schematically illustrated in FIG. 3, additionally having a peripheral donor-side adhesive, and is constructed of the following materials. The donor agent reservoir 16 is composed of 65 weight percent of polyisobutylene and 35 weight percent metoclopramide HCl. The matrix of the counter agent reservoir 22 is composed of 55 weight percent of polyisobutylene, 25 weight percent polyvinylpyrrolidone, 18 weight percent sodium chloride, and 2% sodium phosphate buffer. The donor electrode 11 is silver, while the counter electrode 12 is silver chloride.

The power source component 14 has two 3-volt lithium batteries, such as PANASONIC® model CR 2025 button cell batteries in series. Component 14 further comprises current controlling circuitry, composed of a FET, such as TMPF 4220 (Sprague), and a resistor. Insulator 18 is composed of polyisobutylene. Adhesive layer 24 is composed of POLYCARBOPHIL®.

EXAMPLE II

Another embodiment of the electrotransport system of the present invention has the configuration schematically illustrated in FIG. 4 and is constructed of the following materials. The donor agent reservoir 16 is composed of 55 weight percent of polyisobutylene, 25 weight percent polyvinylpyrrolidone, and 10 weight percent alfentanil hydrochloride. The matrix of the counter agent reservoir 22 is composed of 55 weight percent of polyisobutylene, 25 weight percent polyvinylpyrrolidone, 18 weight percent sodium chloride, and 2% sodium phosphate buffer. The power source for this device is supplied by the galvanic couple formed from contact between the donor and counter elettrodes. Donor electrode 11 is composed of silver, while counter electrode 12 is composed of silver chloride. Insulator 18 is polyisobutylene. Adhesive layer 24 is sodium carboxymethylcellulose.

Having thus generally described our invention and described in detail certain preferred embodiments thereof, it will be readily apparent that various modifications to the invention may be made by workers skilled in the art without departing from the scope of this invention and which is limited only by the following claims.

What is claimed is:

1. A device for delivering a biologically active agent through a body surface by electrotransport, which surface in its natural in vivo state is exposed to a body fluid, said device comprising a plurality of essentially parallel elements, including:
   (a) a counter electrode having an ion-transmitting surface, adjacent said counter electrode, through which ions are transmitted to or from the counter electrode;
   (b) a donor electrode in electrical contact with said counter electrode; and
   (c) a donor reservoir containing said agent to be delivered through said body surface, said donor reservoir being in electrical contact with said donor electrode, said donor reservoir having an ion-transmitting surface through which said agent is transmitted to the body surface, wherein said donor electrode is positioned between said counter electrode and said donor reservoir;
   said device further comprising:
   (d) a means for preventing ion flow along a pathway external to said device and between (i) said donor electrode or said donor reservoir and (ii) said counter electrode, which pathway includes said body fluid and excludes said body surface.

2. A device as recited in claim 1, wherein said ion-transmitting surfaces are major opposing surfaces facing in substantially opposite directions, whereby at least one of said opposing surfaces is adapted to be placed in ion transmitting relation with said body surface.

3. A device as recited in claim 2, further comprising a means for adhering said major opposing surface adapted for ion transfer to said body surface.

4. A device as recited in claim 3, wherein said adhesive means is selected from the group consisting of sodium carboxymethyl cellulose, copolymers of acrylic acid and divinyl glycol, poly(acrylic acid), tragacanth, poly(methyl vinylether co-maleic anhydride), copolymers of acrylic acid and methacrylic acids, and mixtures thereof.

5. A device as recited in claim 2, wherein the surface area of each of said major opposing surfaces is between 1 and 50 $cm^2$.

6. A device as recited in claim 5, wherein the surface area of each of said major opposing surfaces is between 1 and 5 $cm^2$.

7. A device as recited in claim 1, further comprising a counter reservoir comprising an electrolytic salt, said counter reservoir being positioned adjacent said counter electrode, whereby said counter electrode is positioned between said counter reservoir and said donor electrode.

8. A device as recited in claim 1, wherein said means for preventing ion flow comprises an electrical insulating material peripherally contacting said donor electrode and said donor reservoir.

9. A device as recited in claim 1, wherein said device is flexible.

10. A device as recited in claim 1, further comprising an independent power source, positioned between, and in electrical contact with, said donor electrode and said counter electrode.

11. A device as recited in claim 10, wherein said power source comprises at least one battery.

12. A device as recited in claim 1, wherein a galvanic couple is formed between said donor electrode and said counter electrode, thereby generating at least a portion of the power required to operate said device.

13. A device as recited in claim 12, wherein said donor electrode comprises zinc and said counter electrode comprises silver chloride.

14. A device as recited in claim 1, wherein said device is sized to conform generally to human buccal areas.

15. A device as recited in claim 14, wherein said body surface is an mucous membrane in the oral cavity.

16. A device as recited in claim 14, wherein said agent is selected from the group consisting of thymol, cetylpyridinium chloride, benzalkonium chloride, chlorhexidine, stannous fluoride, octenidine, decapinal, triclosan, nystatin, chlortrimazole, fluconazole, miconazole, ketoconazole, itraconazole, amphotericin B, acyclovir, idoxuridine, ibuprofen, flurbiprofen, ketoprofen, naproxen, aspirin, piroxicam, hydrocortisone, betamethasone, dexamethasone, beclomethasone dipropionate, fluocinonide, pilocarpine, and retin A.

17. A device as recited in claim 1, wherein said device is sized to conform generally to sublingual areas.

18. A device as recited in claim 17 wherein said body surface is an mucous membrane in the oral cavity.

19. A device as recited in claim 17, wherein said agent is selected from the group consisting of thymol, cetylpyridinium chloride, benzalkonium chloride, chlorhexidine, stannous fluoride, octenidine, decapinal, triclosan, nystatin, chlortrimazole, fluconazole, miconazole, ketoconazole, itraconazole, amphotericin B, acyclovir, idoxuridine, ibuprofen, flurbiprofen, ketoprofen, naproxen, aspirin, piroxicam, hydrocortisone, betamethasone, dexamethasone, beclomethasone dipropionate, fluocinonide, pilocarpine, and retin A.

20. A method of delivering a biologically active agent from an iontophoretic device through at least one of two facing body surfaces, which body surfaces in their natural in vivo state are exposed to a body fluid, said device including a counter electrode, a donor reservoir containing said agent, and a donor electrode positioned between, and in electrical contact with, said counter electrode and said donor reservoir, said method comprising the steps of:

(1) positioning said device between said facing body surfaces such that an agent-transmitting surface of said device is placed in agent-transmitting relation to one of said body surfaces and a second ion-transmitting surface of said device is placed in ion-transmitting relation with the other body surface;

(2) applying an electrical potential across said body surfaces, wherein an ion transmitting pathway is formed, said pathway including said surfaces of said device and said body surfaces; and (3) electrically insulating said donor reservoir and said donor electrode from body fluid which is in electrical contact with said counter electrode via a pathway external to said body surfaces, thereby substantially preventing ion flow via a pathway through said body fluid and external to said body surfaces.

21. A method as recited in claim 20, further comprising the step of:

(4) adhering said agent-transmitting surface of said device to said body surface which is in agent-transmitting relation with said device.

22. A method as recited in claim 20, wherein said donor electrode and said donor reservoir are sealed from contacting body fluid which is in electrical contact with said counter electrode via a pathway excluding said body surface which is in agent-transmitting relation with said device.

23. A method of delivering a biologically active agent from an iontophoretic device through a body surface, which surface in its natural in vivo state is exposed to a body fluid, said device including a counter electrode, a donor reservoir containing said agent, and a donor electrode positioned between and in electrical contact with said counter electrode and said donor reservoir, said method comprising the steps of:

(1) positioning said device adjacent said body surface such that an agent-transmitting surface of said device is placed in agent-transmitting relation with said body surface, and a second ion-transmitting surface of said device is placed in ion-transmitting relation with said body fluid;

(2) applying an electrical potential across said body surface and said body fluid, wherein an ion transmitting pathway is formed, said pathway including said surfaces of said device and said body surface; and (3) electrically insulating said donor reservoir and said donor electrode from body fluid which is in electrical contact with said counter electrode via a pathway external to said body surface, thereby substantially preventing ion flow via a pathway through said body fluid and external to said body surface.

24. A method as recited in claim 23, further comprising the step of:

(4) adhering said agent-transmitting surface of said device to said body surface which is in agent-transmitting relation with said device.

25. A method as recited in claim 23, wherein said donor electrode and said donor reservoir are sealed from contacting body fluid which is in electrical contact with said counter electrode via a pathway excluding said body surface which is in agent-transmitting relation with said device.

* * * * *